(12) United States Patent
Black

(10) Patent No.: US 7,497,073 B2
(45) Date of Patent: Mar. 3, 2009

(54) ENGINE MONITORING

(75) Inventor: John D. Black, Derby (GB)

(73) Assignee: Rolls-Royce plc, London (GB)

( * ) Notice: Subject to any disclaimer, the term of this patent is extended or adjusted under 35 U.S.C. 154(b) by 357 days.

(21) Appl. No.: 11/453,056

(22) Filed: Jun. 15, 2006

(65) Prior Publication Data
US 2007/0157701 A1 Jul. 12, 2007

(30) Foreign Application Priority Data
Jul. 7, 2005 (GB) .................................. 0513912.6

(51) Int. Cl.
*F02G 3/00* (2006.01)
*F02C 6/00* (2006.01)

(52) U.S. Cl. ...................................... 60/39.091; 60/803

(58) Field of Classification Search ................... 60/39.5, 60/264, 770, 39.091, 803; 73/23.31; 356/317, 356/318, 417; 250/339.05, 339.14
See application file for complete search history.

(56) References Cited

U.S. PATENT DOCUMENTS 3,677,650 A * 7/1972 Klingler ..................... 356/338

4,147,431 A * 4/1979 Mann ........................... 356/72
5,024,055 A * 6/1991 Sato et al. ................... 60/39.27
5,461,855 A * 10/1995 Inoue et al. ................... 60/776

FOREIGN PATENT DOCUMENTS

| DE | 199 44 006 A 1 | 3/2001 |
|---|---|---|
| EP | 0 881 373 A3 | 12/1998 |
| EP | 0 985 921 A1 | 3/2000 |
| GB | 1141125 | 1/1969 |
| JP | A 2005-024250 | 1/2005 |

* cited by examiner

*Primary Examiner*—Michael Cuff
*Assistant Examiner*—Vikansha S Dwivedi
(74) *Attorney, Agent, or Firm*—Oliff & Berridge, PLC

(57) ABSTRACT

Continuous engine monitoring with regard to gas turbine engines is difficult particularly when the engine is utilized for propulsion of an aircraft. Nevertheless, by use of transfer passages 4 to an arrangement located within the tail cone 9 of an engine, it is possible through a transparent test cell 6 and appropriate heating to generate sufficient infra red radiation as well as incandescent visible light for detectors 11, 16 to determine various constituent parts of the gas flow. Thus a photo detector 11 can provide through electrical signals, the proportion of soot/smoke particles in the gas flow through their incandescence, whilst use of filters 17 for particular spectral lines in an infra red radiation spectrum will allow detectors 16 to provide an indication through an electrical signal the proportion and presence of other constituents such as NO, CO and unburnt hydrocarbons in an exhaust gas flow.

24 Claims, 1 Drawing Sheet

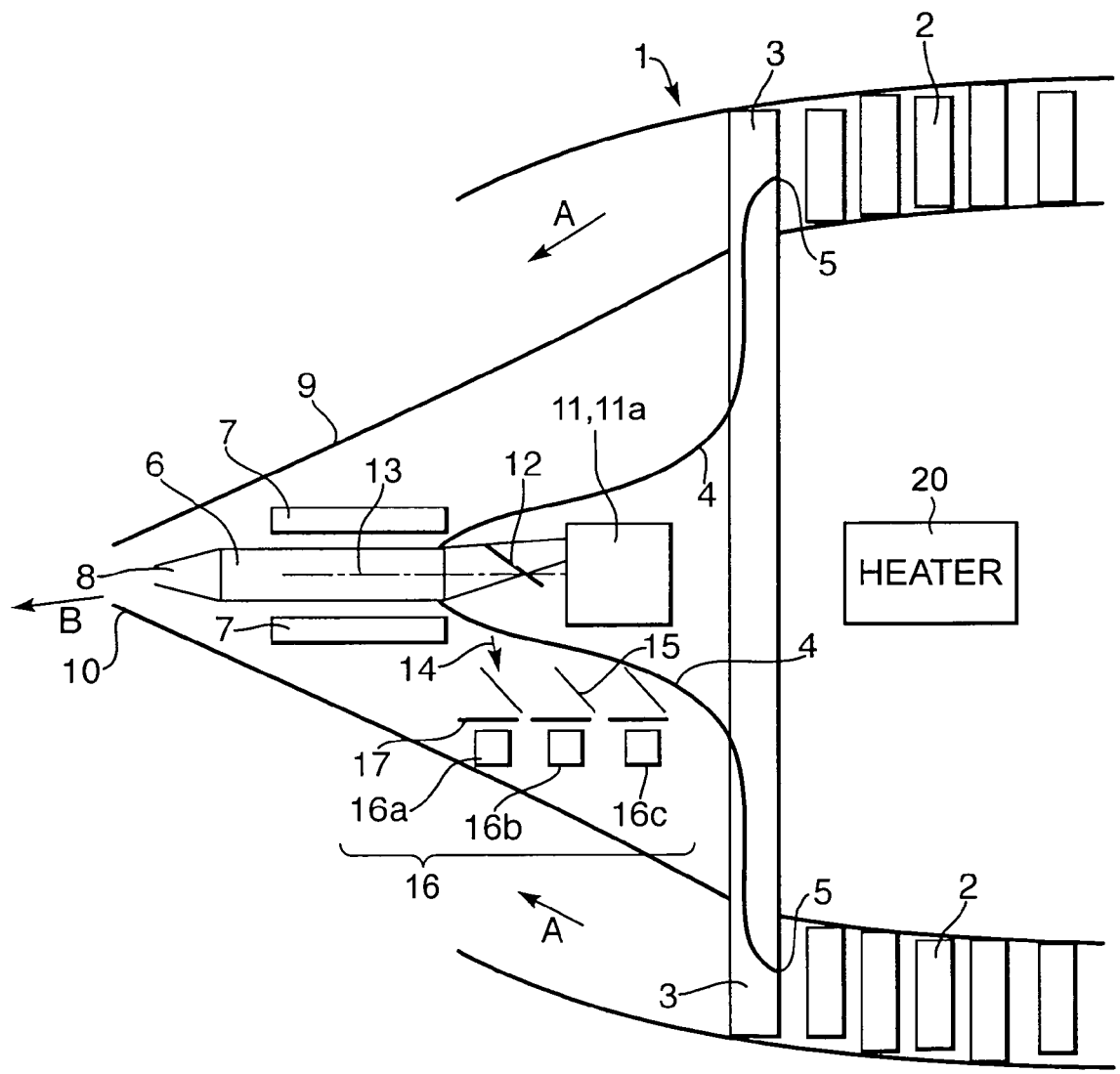

ENGINE MONITORING

BACKGROUND

The present invention relates to engine monitoring and more particularly to monitoring of gas turbine engines utilised with respect to aircraft propulsion.

It is important with respect to engine operation and particularly with regard to gas turbine engine operation to monitor various component parts of the exhaust gases from the engine. These component parts generally indicate the efficiency with respect to engine operation and ensure that engine operation remains within acceptable environmental and regulatory authority limits. It will be appreciated that engine monitoring can be performed either continuously or during engine set up or during a calibration stage. Ideally, engine monitoring should be continuous but it will be understood particularly with regard to gas turbine engines operated with respect to aircraft propulsion that the additional weight of monitoring equipment and also space constraints limit the possibility with respect to continuous engine monitoring.

Currently, exhaust emissions measurements are carried out by sampling exhaust gas with probes or rakes mounted behind an engine on a test bed. The samples taken are transferred to a number of measuring instruments outside of the test bed presentation of the engine. Clearly, such an approach does not lend itself to ongoing engine monitoring and furthermore the transfer of the samples taken from the test bed presentation of the engine may alter the results provided.

In the above circumstances, non intrusive analytical techniques for monitoring engine exhaust emissions are being devised or utilised with respect to engine test bed operations. These non intrusive approaches incorporate use of spectroscopic and laser induced incandescence in the exhaust plume such that the emitted infra red and incandescence can be measured by an appropriate spectrometer. Packaging such non intrusive systems into an engine requires great care to avoid excessive weight and for space utilisation.

SUMMARY

In accordance with the present invention there is provided an engine monitoring arrangement for mounting within a gas turbine engine, the arrangement comprising a transparent test cell having a photo luminescence exciter and associated with a photo detector arrangement, the arrangement presents a test gas flow to the transparent test cell for photo luminescent excitation by the photo luminescent exciter so that in use the photo luminescent response can be determined by the photo detector arrangement.

Normally, the test gas flow is presented through a transfer pipe arranged to sample exhaust gas flow to provide the test gas flow.

Typically, the photo detector arrangement comprises a visible wavelength detector and/or at least one infra red detector. Normally, the photo detector arrangement includes a photo radiation filter for a particular gas constituent expected within the test gas flow. Generally, the particular gas constituent is soot or carbon monoxide or nitrogen oxide or unburnt hydrocarbon. Possibly, it is advantageous to monitor carbon dioxide ($CO_2$)/water ($H_2O$) for efficiency measurement and formaldehyde ($H_2CO$). Generally, the photo detector arrangement provides at least one photo detector path including the photo radiation filter for each particular gas constituent monitored in use by the engine monitoring arrangement.

Possibly, the test cell is heated to enhance inherent photo radiation and particularly infra red radiation provided by the test gas flow in the test cell.

Generally the photo luminescent exciter comprises a diode laser or flash lamp. Generally the photo luminescent exciter surrounds the transparent test cell.

Normally, the test cell is open ended to facilitate continuous test gas flow in use through the test cell.

Generally, the photo detector arrangement is associated with or incorporates a deflector for guiding photo radiation to a specific photo detector in the monitoring arrangement. Possibly, the specific photo detector arrangement is generally upstream of the major axis of the test cell. Alternatively, the specific photo detector is arranged to one side of the major axis of the test cell.

Generally, the transfer pipe incorporates means to draw off the test gas flow. Possibly, the transfer pipe is associated with control means to periodically open the transfer pipe to allow the test gas flow to the test cell. Possibly, the control means controls the photo luminescent exiter for adjustment of photo radiance as required for test gas flow monitoring.

Additionally, in accordance with the present invention there is provided a gas turbine engine incorporating an engine monitoring arrangement as described above, the engine including a tail cone and the engine monitoring arrangement accommodated in the tail cone. Generally, an outlet for the test cell is arranged towards an end of the tail cone to facilitate gas flow through the test cell.

BRIEF DESCRIPTION OF THE DRAWINGS

The FIGURE is a schematic illustration of a gas turbine engine including a monitoring arrangement according to the present invention.

DETAILED DESCRIPTION OF EMBODIMENTS

An embodiment of the present invention will now be described by way of example and with reference to the accompanying drawing showing a schematic cross section of a tail cone end of a gas turbine engine incorporating an engine monitoring arrangement.

As indicated above, on line or real time exhaust gas analysis from a gas turbine engine would be of real benefit. However, previously such arrangements have tended to be too detrimental in terms of additional weight as well as necessary space for accommodation to be acceptable particularly with regard to aircraft engines. The description below will principally be directed towards use of an engine monitoring arrangement in relation to aircraft engines, but a monitoring arrangement could equally be applied to marine or stationary gas turbine engines or even internal combustion engines where the exhaust gas flow must be analysed for continuing performance. The present engine monitoring arrangement is of a relatively small size and low weight providing the desired acceptability over conventional monitoring instruments used in aeroengines.

Typically the species which are required to be measured in an aero engine gas monitoring arrangement are carbon monoxide (CO), nitrogen oxide (NO), nitrogen dioxide ($NO_2$), unspecified unburnt hydrocarbon (UHC) and smoke/soot. Thus, there are a range of gas flow constituents which must be analysed in most situations whether for simple engine efficiency determination or for certification of acceptability of the engine for operation in a particular jurisdiction.

The present engine monitoring arrangement comprises a relatively compact combination of components which can be located within the tail cone of an engine. A test cell is formed to receive a test gas flow which passes through the test cell and out of the tail cone on the engine. Exhaust gas is sampled in a test gas flow presented through the test cell. This test gas flow is generally sampled from the final engine stages about the guide vanes and transferred through a transfer pipe to the test cell for through flow and monitoring through analysis as described above and below. Generally the transfer pipes are heated to retain gas temperature during transmission such that the monitoring process is non intrusive. It will be appreciated that as the test gas flow passes through the transfer pipes it may cool and therefore the constituent components vary in proportions from that in the actual exhaust gas flow of the engine. Heating in the transfer lines is substantially to maintain test gas flow temperature against the prospect of cooling.

The test gas flow entering the test cell is clearly already at a high temperature when scooped from the exhaust gas flow. The test cell will also further generally heat the test gas flow to enhance emission of infra red radiation. The emitted infra red radiation is detected by respective infra red detectors for particular constituent parts. Generally, each infra red detector will be associated in a detector path with an appropriate infra red filter. The infra red filters are specific and pass infra red radiation spectral lines associated only with their specific constituent part, that is to say NO, CO and UHC respectively. At temperatures greater than 800° C., nitrogen dioxide ($NO_2$) will decompose to form nitrogen oxide. Thus, if the test cell increases the test gas flow to such temperatures the proportion of nitrogen oxide will increase and this can be utilised in order to extrapolate the proportion of nitrogen dioxide in the test gas flow and therefore the actual gas flow from the engine. As an alternative an optical grating could be used to disperse the infra red spectrum onto a grating spectrometer detector able to detect the respective spectral lines associated with the specific gas flow components, that is to say NO, CO and UHC. However, provision of such a grating spectrometer particularly with regard to aeroengine usage would be generally more expensive.

The test cell is formed from an appropriate transparent material such that light from photo luminescent exciters such as diode laser bars or flash lamps mounted outside the cell parallel to the major axis of the test cell can induce incandescence with regard to soot/smoke particles in the test gas flow. Such incandescence will create visible incandescent light which is collected along the major axis of the test cell and focused upon an appropriate photo detector such that the incandescent signal observed by that photo detector is proportional to the soot volume fraction in the test gas flow in order to provide an indication of smoke within the test gas flow.

At its basic level the present engine monitoring arrangement simply comprises transfer pipes for delivery of the test gas flow to the test cell. This test gas flow as indicated radiates infra red radiation such that an infra red photo detector can determine a constituent part within the test gas flow. However, normally as indicated, a number of constituents within the test gas flow will be investigated by the engine monitoring arrangement so that generally there are a number of photo detectors as indicated, one detector for visible incandescent light and a number of infra red photo detectors for particular spectral lines of infra red radiation indicative of the constituent parts, that is to say NO, CO and UHC in the test gas flow.

The photo detectors utilised in accordance with the present invention will be provided with electrical power from the normal electrical power loom within an engine. Similarly, heating for the test cell as well as any heating provided in the transfer pipes may also be provided by heating elements powered by electrical energy derived from the engine.

Ongoing continuous engine monitoring as indicated is desirable, but alternatively a control device could be utilised such that engine sampling occurs periodically or upon specific requests. In either event the transfer pipe would be opened such that a scoop end portion of the inlet pipe will collect a test gas flow for transmission to the test cell. It will also be understood that this control may adjust the heating or photo luminescence exciter elements within the arrangement appropriately to achieve best monitoring results.

A particular engine monitoring arrangement in accordance with the present approach is schematically illustrated in the attached drawing. Thus, an engine 1 includes a turbine assembly 2 with outlet guide vanes 3 arranged such that in a leading edge of that outlet guide vane 3 a transfer pipe or pipes 4 is presented to scoop gas flow in the direction of arrowheads A from the engine. The transfer pipes 4 lead from a scoop entry 5 to a test cell 6. The transfer pipe 4 as indicated above may be heated by heater 20 in order to maintain test gas flow temperature during transfer along the transfer pipe 4.

The test cell 6 is formed from a transparent body. The test cell 6 will also be generally heated in order to create photo luminescence and incandescence in the test gas flow passing through the cell 6 in the direction of arrowhead B.

Either side of the test cell 6, photo luminescent exciters 7 are utilised either to enhance infra red emissions or simply to illuminate the incandescent light from the soot created by heating within the cell 6.

As indicated there is a general exhaust gas flow along the transfer pipes 4 through the cell 6 and out of an ejector 8. In such circumstances a constant flow through the engine monitoring arrangement is achieved for appropriate monitoring of the gas flow in the direction of arrowhead A. The representative sample is in the form of this continuous test gas flow passing through the transfer pipe 4 to the test cell 6. It will be understood that the rate of this flow through the engine monitoring arrangement may be adjusted by some form of valve in the transfer pipe 4 whilst dwell within the cell 6 may be adjusted by varying the outlet orifice cross section of the ejector 8. Nevertheless, it will be noted that the present engine management arrangement is substantially contained within a tail cone 9 of the engine so that accommodation within the engine is not difficult. Furthermore, the component parts as described above and later are relatively light and will not significantly add to engine weight.

Test gas flow through the pipes 4 and cell 6 out of the ejector 8 may be stimulated by adjacent engine major propulsion flow in the direction of arrowhead A through a Venturi effect drawing the test gas flow through the engine monitoring arrangement and out of the ejector 8 and subsequently an end 10 of the engine tail cone 9. The test cell 6 is effectively open ended with the ends of the transfer pipes entering at one end whilst the ejector 8 provides an open end to the test cell 6 at the other.

The heating as well as the illumination/excitation provided by the diode laser bars or flash lamps, which are examples of photo luminescent exciters 7, as indicated creates incandescence in the soot or smoke particles in the test gas flow. This incandescence is detected by a photo detector 11, which includes visible wavelength detector 11*a*, generally upstream of the cell 6. The visible illumination created by the incandescent soot or smoke particles is focused upon the detector 11. In such circumstances the level of electrical signal generated by the detector 11 is proportional to the soot/smoke particle fraction within the test gas flow and hence should provide a measure of the smoke/soot within the engine major propulsion flow in the direction of arrowheads A. The means for focusing the incandescent visible light under the detector 11 is provided by an appropriate light collector and focusing element 12. The general direction of the incandescent light is indicated by broken line 13 and in a direction towards the detector 11, but it will be appreciated that the visible incandescent light as well as infra red radiation will be emitted in all directions. Nevertheless, the focusing element 12 will also direct particularly the infra red radiation downwards as depicted to an infra red detector array comprising a number of individual infra red detectors. The general direction of this infra red radiation deflection is given by arrowhead 14 but will normally be radial in all directions.

The infra red radiation generally given in the direction of arrowhead 14 is itself cascaded by deflectors 15 to become incident upon the respective detectors 16a, 16b, 16c. Each one of these infra red detectors 16 will be associated with a specific respective IR filter 17. Each IR filter 17 will be arranged to pass only a spectral line or band associated with a particular gas flow constituent, e.g. NO, CO and UHC. In such circumstances, the incident infra red radiation upon each detector 16 will be proportionate and indicative of the particular constituent associated with its IR filter 17. In such circumstances each deflector 15, filter 17 and detector 16 creates a photo detector path for a particular gas constituent.

As an alternative a grating spectrometer could be provided in which the infra red radiation 14 is diffracted by an optical grating upon the spectrometer such that the spectral lines are incident upon different parts of the spectrometer and therefore the spectral trace provides an indication as to the constituent part proportions and presence within the test gas flow and therefore the gas flow through the engine. It will be understood that the tail cone 9 within the engine will also generally accommodate the bearing housings for shafts upon which the turbines and other rotating machinery of the engine are supported. Nevertheless as indicated the space requirements for the cell 6 as well as the transfer pipes and detectors 11, 16 will be relatively small and therefore easy to accommodate within the tail cone. By use of the existing electrical power capability of the engine as indicated,. the test cell 6 is heated in order to increase infra red radiation for deflection appropriately to the detector 16 whilst the electrical power can also be utilised in order to provide the excitation achieved by this heating and use of diode laser bars and flash lamps.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

I claim:

1. A gas turbine engine incorporating an engine monitoring arrangement mounted within the gas turbine engine, the gas turbine engine including a tail cone, the engine monitoring arrangement being mounted in the tail cone, the engine monitoring arrangement comprising a transparent test cell, a photo luminescent exciter and a photo detector arrangement, the engine monitoring arrangement comprising at least one transfer pipe to supply a test gas flow to the transparent test cell for photo luminescent excitation by the photo luminescent exciter so that in use the photo luminescent response can be determined by the photo detector arrangement.

2. A gas turbine engine as claimed in claim 1 wherein the transfer pipe is arranged to sample exhaust gas flow from the gas turbine engine to provide the test gas flow.

3. A gas turbine engine as claimed in claim 1 wherein the photo detector arrangement comprises a visible wavelength detector and at least one infra red detector.

4. A gas turbine engine as claimed in claim 1 wherein the at least one infra red detector includes at least one infra red radiation filter for a particular gas constituent expected within the test gas flow.

5. A gas turbine engine as claimed in claim 4 wherein the at least one infra red detector comprises a plurality of infra red detectors, each infra red detector includes an infra red radiation filter for a particular gas constituent monitored in use by the engine monitoring arrangement.

6. A gas turbine engine as claimed in claim 5 wherein the plurality of infra red detectors monitor for infra red radiation from particular gas constituents carbon monoxide, nitrogen oxide and unburnt hydrocarbon.

7. A gas turbine engine as claimed in claim 1 wherein the test cell has a heater to enhance inherent photo radiation and infra red radiation in the test gas flow in the test cell.

8. A gas turbine engine as claimed in claim 3 wherein the visible wavelength detector monitors for incandescent light from soot or smoke.

9. A gas turbine engine as claimed in claim 1 wherein the photo luminescent exciter comprises a diode laser or flash lamp.

10. A gas turbine engine as claimed in claim 1 wherein the photo luminescent exciter surrounds the transparent test cell, 11. A gas turbine engine as claimed in claim 1 wherein the test cell is open ended to facilitate continuous test gas flow in use through the test cell.

12. A gas turbine engine as claimed in claim 1 wherein the photo detector arrangement incorporates at least one deflector for guiding photo radiation to a specific photo detector in the monitoring arrangement.

13. A gas turbine engine as claimed in claim 12 wherein the specific photo detector arrangement is generally upstream of the major axis of the test cell.

14. A gas turbine engine as claimed in claim 12 wherein the specific photo detector is arranged to one side of the major axis of the test cell.

15. A gas turbine engine as claimed in claim 1 wherein the transfer pipe incorporates means to draw off the test gas flow.

16. A gas turbine engine as claimed in claim 1 wherein the transfer pipe is associated with control means to periodically open the transfer pipe to allow the test gas flow to the test cell.

17. A gas turbine engine as claimed in claim 16 wherein the control means controls the photo luminescent exciter for adjustment of photo radiance as required for test gas flow monitoring.

18. A gas turbine engine as claimed in claim 1 wherein an outlet of the test cell is arranged towards an end of the tail cone to facilitate gas flow through the test cell.

19. A gas turbine engine as claimed in claim 18 wherein the outlet of the test cell includes an ejector to draw the test gas flow through the end of the tail cone.

20. A gas turbine engine as claimed in claim 1 where the at least one transfer pipe has a heater to heat the test gas flow.

21. A gas turbine engine as claimed in claim 1 wherein the turbine engine comprise a turbine assembly, the turbine assembly being arranged upstream of the tail cone, the turbine assembly including outlet guide vanes having leading edges, the at least one transfer pipe extending through an outlet guide vane.

22. A gas turbine engine as claimed in claim 21 wherein the at least one transfer pipe having a scoop entry in the leading edge of an outlet guide vane.

23. An engine monitoring arrangement, the engine monitoring arrangement comprising a transparent test cell, a photo luminescent exciter and a photo detector arrangement, the engine monitoring arrangement comprising at least one transfer pipe to supply a test gas flow to the transparent test cell for photo luminescent excitation by the photo luminescent exciter so that in use the photo luminescent response can be determined by the photo detector arrangement and wherein the test cell having a heater to enhance inherent photo radiation and infra red radiation in the test gas flow in the test cell.

24. An engine monitoring arrangement, the engine monitoring arrangement comprising a transparent test cell, a photo luminescent exciter and a photo detector arrangement, the engine monitoring arrangement comprising at least one transfer pipe to supply a test gas flow to the transparent test cell for photo luminescent excitation by the photo luminescent exciter so that in use the photo luminescent response can be determined by the photo detector arrangement and wherein the photo luminescent exciter surrounds the transparent test cell.

* * * * *